(12) United States Patent
Dassler et al.

(10) Patent No.: US 9,074,230 B2
(45) Date of Patent: Jul. 7, 2015

(54) METHOD FOR PRODUCING L-CYSTINE BY FERMENTATION UNDER CONTROLLED OXYGEN SATURATION

(75) Inventors: Tobias Dassler, Munich (DE); Anneliese Reutter-Maier, Kirchseeon (DE); Thomas Schloesser, Burghausen (DE)

(73) Assignee: Wacker Chemie AG, Munich (DE)

( * ) Notice: Subject to any disclaimer, the term of this patent is extended or adjusted under 35 U.S.C. 154(b) by 0 days.

(21) Appl. No.: 14/116,049

(22) PCT Filed: May 4, 2012

(86) PCT No.: PCT/EP2012/058175
§ 371 (c)(1),
(2), (4) Date: Nov. 6, 2013

(87) PCT Pub. No.: WO2012/152664
PCT Pub. Date: Nov. 15, 2012

(65) Prior Publication Data
US 2014/0080186 A1 Mar. 20, 2014

(30) Foreign Application Priority Data
May 11, 2011 (DE) .......................... 10 2011 075 656

(51) Int. Cl.
*C12P 13/12* (2006.01)
(52) U.S. Cl.
CPC ...................................... *C12P 13/12* (2013.01)
(58) Field of Classification Search
None
See application file for complete search history.

(56) References Cited

U.S. PATENT DOCUMENTS

| | | | |
|---|---|---|---|
| 5,972,663 | A | 10/1999 | Winterhalter et al. |
| 6,218,168 | B1 | 4/2001 | Leinfelder et al. |
| 2004/0038352 | A1 | 2/2004 | Maier |
| 2005/0009162 | A1 | 1/2005 | Maier et al. |
| 2005/0221453 | A1 | 10/2005 | Takagi et al. |
| 2009/0053778 | A1 | 2/2009 | Sauer et al. |
| 2009/0226984 | A1 | 9/2009 | Nonaka et al. |

FOREIGN PATENT DOCUMENTS

| | | |
|---|---|---|
| CA | 2386539 A1 | 4/2002 |
| EP | 0235908 A2 | 9/1987 |
| EP | 0620853 B1 | 3/1996 |
| EP | 0885962 A1 | 12/1998 |
| EP | 0931833 A2 | 7/1999 |
| EP | 1389427 A1 | 2/2004 |
| EP | 1496111 A2 | 1/2005 |
| EP | 1571223 A2 | 9/2005 |
| EP | 2138585 B1 | 2/2011 |
| WO | 2004113373 A1 | 12/2004 |

OTHER PUBLICATIONS

N. M. Kredich, editors: F. C. Neidhardt, R. Curtiss III, J. L. Ingraham, E. C. C. Lin, K. B. Low, B. Magasanik, W. S. Reznikoff, M. Riley, M. Schaechter, and H. E. Umbarger, "Biosynthesis of Cysteine", *Escherichia coli* and *Salmonella*: cellular and molecular biology, 1996, pp. 514-527, 2nd edition, ASM Press, Washington, D.C.
S. Nakamori et al., Overproduction of L-Cysteine and L-Cystine by *Escherichia coli* Strains with a Genetically Altered Serine Acetyltransferase, Applied and Environmental Microbiology, 1998, pp. 1607-1611, vol. 64, No. 5; American Society for Microbiology.
H. Takagi et al., PCR Random Mutagenesis into *Escherichia coli* Serine Acetyltransferase: Isolation of the Mutant Enzymes that Cause Overproduction of L-cysteine and L-cystine due to the Desensitization to Feedback Inhibition, FEBS Letters 452, 1999, pp. 323-327.
M. K. Gaitonde, A Spectrophotometric Method for the Direct Determination of Cysteine in the Presence of Other Naturally Occuring Amino Acids, Biochem J. 1967, pp. 627-633, vol. 104.
S. Kumon et al., Simultaneous Oxidative Reaction Crystallization of L-cystine from L-cysteine with Enzyme Reactions of DL-amino-thiazoline-carboxylic Acid as Feed Material, Food and Bioproducts Processing: Transactions of the Institution of Chemical Engineers, 1994, pp. 86-90, vol. 72, No. 2.
English abstract for G. E. Jeromin et al., "Bioorganikum Praktikum der Biokatalyse", 2005, pp. 1-13, Wiley-VCH Verlag GmbH & Co. KGaA, Weinheim, Germany.
International Search Report for PCT/EP2012/058175 dated Jul. 4, 2012.

*Primary Examiner* — Alexander Kim
(74) *Attorney, Agent, or Firm* — Caesar Rivise, PC

(57) ABSTRACT

The invention relates to a method for producing L-cystine by fermenting a microorganism strain in a fermentation medium, in which method L-cystine is precipitated in an amount of at least 70% relative to the total cysteine, characterized in that the $O_2$ saturation of the fermentation medium is kept at least at 1% and at most at 40±3% during the formation of L-cystine.

17 Claims, No Drawings

METHOD FOR PRODUCING L-CYSTINE BY FERMENTATION UNDER CONTROLLED OXYGEN SATURATION

BACKGROUND OF THE INVENTION

The invention relates to a method for producing L-cystine by fermentation.

L-cystine is a disulfide which is formed by the oxidation of two molecules of L-cysteine. This reaction is reversible, which means that L-cystine may be reconverted to L-cysteine by reduction.

The amino acid L-cysteine is of economic significance. It is used, for example, as a food additive (particularly in the baking industry), as a feedstock in cosmetics, and also as a starting product for preparing active pharmaceutical ingredients (particularly N-acetylcysteine and S-carboxymethylcysteine).

L-cysteine plays a key role in sulfur metabolism in all organisms and is used in the synthesis of proteins, glutathione, biotin, lipoic acid, methionine and other sulfur-containing metabolites. In addition, L-cysteine serves as precursor for the biosynthesis of coenzyme A. The biosynthesis of L-cysteine has been investigated in depth in bacteria, particularly in Enterobacteria, and is described in detail in Kredich (1996, Biosynthesis of cysteine, pp. 514-527. In F. C. Neidhardt, R. Curtiss III, J. L. Ingraham, E. C. C. Lin, K. B. Low, B. Magasanik, W. S. Reznikoff, M. Riley, M. Schaechter, and H. E. Umbarger (ed.), *Escherichia coli* and *Salmonella*: cellular and molecular biology, 2nd ed. ASM Press, Washington, D.C.).

In addition to the classical production of L-cysteine by means of extraction from keratin-containing material such as hair, bristles, horns, hooves and feathers or by means of biotransformation by enzymatic conversion of precursors, a method for producing L-cysteine by fermentation was also developed some years ago. The prior art with respect to the production of L-cysteine by fermentation using microorganisms has been described in detail e.g. in U.S. Pat. Nos. 6,218,168B1, 5,972,663A, U.S.2004/0038352A1, CA2386539A1, U.S.2009/0053778A1 and U.S.2009/0226984A1. The bacterial host organisms used here are, inter alia, strains of the genus *Corynebacterium* and also representatives from the *Enterobacteriaceae* family such as *Escherichia coli* or *Pantoea ananatis*.

In addition to the classical procedure of attaining improved L-cysteine producers by mutation and selection, specific genetic modifications to the strains have also been carried out in order to achieve an effective L-cysteine overproduction.

The insertion of a cysE allele coding for a serine O-acetyl transferase having a reduced feedback inhibition by L-cysteine thus led to an increase in cysteine production (U.S. Pat. No. 6,218,168B1; Nakamori et al., 1998, Appl. Env. Microbiol. 64: 1607-1611; Takagi et al., 1999, FEBS Lett. 452: 323-327). By means of a feedback-resistant CysE enzyme, the formation of O-acetyl-L-serine, the direct precursor of L-cysteine, is largely decoupled from the L-cysteine level in the cell.

O-acetyl-L-serine is formed from L-serine and acetyl-CoA. Thus, the provision of L-serine in sufficient amounts for L-cysteine production is of major importance. This may be achieved by insertion of a serA allele coding for a 3-phosphoglycerate dehydrogenase having a reduced ability for feedback inhibition by L-serine. The formation of 3-hydroxy-pyruvate, a precursor of L-serine, is thereby largely decoupled from the L-serine level in the cell. Examples of such SerA enzymes have been described in EP0620853, U.S. 2005/0009162 A1, U.S.2005009162A2 and EP0931833.

It is further known that the L-cysteine yield in the fermentation may be increased by weakening or destroying genes coding for L-cysteine-degrading enzymes, such as the tryptophanase TnaA or the cystathionine-(β-lyases MalY or MetC (EP1571223).

The increase of the transport of L-cysteine out of the cell is a further possibility to increase the product yield in the medium. This may be achieved by overexpression of so-called efflux genes. These genes code for membrane-bound proteins which mediate the export of L-cysteine from the cell. Various efflux genes for L-cysteine export have been described (U.S. Pat. No. 5,972,663A, U.S.2004/0038352A1, U.S.2005221453, WO2004113373).

The export of L-cysteine from the cell into the fermentation medium has several advantages:

1) L-cysteine is continuously abstracted from the intracellular reaction equilibrium with the result that this amino acid is maintained at a low level in the cell and there is therefore no feedback inhibition of sensitive enzymes by L-cysteine:

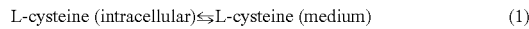

L-cysteine (intracellular)⇌L-cysteine (medium)    (1)

2) The L-cysteine released into the medium is oxidized to the disulfide L-cystine in the presence of oxygen, which is introduced into the medium during the cultivation (U.S. Pat. No. 5,972,663A):

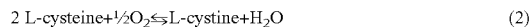

2 L-cysteine+½O₂⇌L-cystine+H₂O    (2)

Since the solubility of L-cystine in aqueous solution at a neutral pH is only very low, especially in comparison to L-cysteine, the disulfide precipitates even at a low concentration and forms a white precipitate:

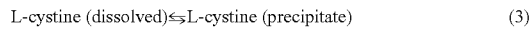

L-cystine (dissolved)⇌L-cystine (precipitate)    (3)

Through the precipitation of L-cystine, the level of the product dissolved in the medium is reduced, whereby the reaction equilibrium of (1) and (2) in each case is also drawn to the product side.

3) The technical effort for the purification of the product is considerably lower if the amino acid can be obtained directly from the fermentation medium than when the product accumulates intracellularly and an initial cell lysis has to be carried out.

Facultative anaerobic bacteria, such as *E. coli* or *P. ananatis*, grow better under aerobic conditions, i.e. in the presence of oxygen, since they can obtain more energy from carbohydrates such as glucose by aerobic metabolism than by fermentation (anaerobic metabolism) of the respective energy source.

L-cysteine production using *E. coli* or *P. ananatis* is also carried out under aerobic conditions (U.S.2004/0038352A1, U.S. Pat. No. 5,972,663A, CA2386539A1, EP1389427, EP2138585). It is disclosed in the methods described in more detail that the oxygen input into the culture is adjusted such that the culture broth has an oxygen content of 50% during the fermentation.

A disadvantage of the methods described for the production of L-cysteine by fermentation is that the amino acid is present in the culture broth in various forms. In addition to the precipitated L-cystine in the precipitate, L-cystine in dissolved form and also L-cysteine and also a thiazolidine are found in the culture supernatant (U.S. Pat. Nos. 6,218,168B1, 5,972,663A, CA2386539A1). This thiazolidine (2-methylthiazolidine-2,4-dicarboxylic acid) is the condensation product of L-cysteine and pyruvate, which is formed in a purely chemical reaction.

The term "total cysteine" in the context of this invention combines L-cysteine and the L-cystine and thiazolidine compounds formed therefrom, which are formed during the fermentation and accumulate in the culture supernatant and in the precipitate.

In the known methods, the proportion of precipitated L-cystine varies at the end of the fermentation. This is between 40-66% (U.S. Pat. No. 5,972,663A, CA2386539A1) of the total cysteine, which means that the residual 34-60% of the total cysteine is present in the culture supernatant, namely predominantly in the form of L-cysteine and thiazolidine. This product heterogeneity hinders the recovery and purification of the product from the culture broth.

A method is therefore desirable in which the end product mostly occurs in only one form. Particularly favorable is a method in which L-cystine is predominantly formed as product, since L-cystine precipitates even at a low concentration due to its low solubility in a pH neutral aqueous medium, whereby the reaction equilibrium is shifted to the product side, which in turn leads to relatively high product yields.

DESCRIPTION OF THE INVENTION

It is accordingly an object of the present invention to provide a method for producing L-cystine by means of fermenting a microorganism strain in a fermentation medium, in which method L-cystine precipitates in an amount of at least 70% relative to the total cysteine formed.

The object is achieved by a method which is characterized in that the $O_2$ saturation of the fermentation medium during the formation of L-cystine is maintained at least at 1% and at most at 40±3%.

The $O_2$ saturation of the medium is defined as the proportion of the dissolved oxygen amount as a percentage of the maximum soluble oxygen amount under the stated conditions.

It was shown, surprisingly, that the precipitated L-cystine as a proportion of the total cysteine in the culture broth at the end of the fermentation is at least 70% (weight per liter of precipitated L-cystine to weight per liter of total cysteine), if the $O_2$ saturation is maintained in this low range. This finding is astonishing, in particular since EP1389427 discloses that a high L-cystine proportion may actually be achieved by introducing an oxidizing agent, e.g. in the form of oxygen or hydrogen peroxide, in an increased amount into the culture.

The method according to the invention is also very advantageous since purification of the product is readily achieved as the L-cystine present as a precipitate can be separated from the cells by a simple decanting step.

The cystine formation phase of the fermentation method according to the invention starts from the time point at which the L-cystine can be detected for the first time as a precipitate in the culture broth and continues until the end of the cultivation. Typically, this phase starts ca. 8-10 h after inoculation of the production fermenter.

The microorganisms which may be used in the method according to the invention are all cysteine-producing strains described in the prior art. Such strains are disclosed, for example, in U.S. Pat. Nos. 6,218,168B1, 5,972,663A, U.S.2004/0038352A1, CA2386539A1, U.S.2009/0053778 or EP2138585.

Preferred microorganisms are representatives from the Enterobacteriaceae family, particularly preferably representatives of the genera *Escherichia* and *Pantoea*, especially preferably strains of the *E. coli* and *P. ananatis* species.

Among these microorganism strains, preference is given in turn to strains which either have a modified serine O-acetyltransferase, which has a feedback inhibition by L-cysteine reduced by at least a factor of 2 in comparison to the corresponding wild type enzyme, or which have a cysteine export from the cell increased by at least a factor of 2 by overexpression of an efflux gene in comparison to a wild type cell. Particular preference is given to microorganism strains having both a serine O-acetyltransferase having a feedback inhibition by L-cysteine reduced by at least a factor of 2 in comparison to the corresponding wild type enzyme and a cysteine export from the cell increased by at least a factor of 2 by overexpression of an efflux gene in comparison to a wild type cell. Such strains are known, for example, from U.S. Pat. Nos. 6,218,168B1 and 5,972,663A. Especially preferred strains are those which additionally have a modified 3-phosphoglycerate dehydrogenase having a feedback inhibition by L-serine reduced by at least a factor of 2 in comparison to the corresponding wild type enzyme (U.S. 2005/0009162A1, U.S.2005009162A2) and in which at least one L-cysteine-degrading enzyme has been weakened insofar as at most only 50% of this enzyme activity is present in the cell in comparison to a wild type cell.

Preferred variants of the serine O-acetyltransferase have a feedback inhibition by L-cysteine reduced by at least a factor of 5, particularly preferably by at least a factor of 10, especially preferably by at least a factor of 50, in comparison to the corresponding wild type enzyme.

The efflux gene preferably originates from the ydeD (see U.S. Pat. No. 5,972,663A), yfiK (see U.S.2004/0038352A1), cydDC (see WO2004113373), bcr (see U.S.2005221453) and emrAB (see U.S.2005221453) group of *E. coli* or the corresponding homologous gene from another microorganism. A homologous gene is understood to mean that the sequence of this gene corresponds to an extent of at least 80% to the DNA sequence of the corresponding *E. coli* gene.

The overexpression of an efflux gene preferably leads to a cysteine export from the cell increased by at least a factor of 5, particularly preferably by at least a factor of 10, particularly preferably by at least a factor of 20, in comparison to a wild type cell.

Preferred variants of the 3-phosphoglycerate dehydrogenase have a feedback inhibition by L-serine reduced by at least a factor of 5, particularly preferably by at least a factor of 10, especially preferably by at least a factor of 50, in comparison to the corresponding wild type enzyme.

The L-cysteine-degrading enzyme preferably originates from the group of tryptophanase (TnaA) and cystathionine-β-lyase (MalY, MetC).

Particular preference is given to microorganism strains in which at least one of these enzymes has been weakened insofar as at most only 10% of the enzyme activity is still present in the cell in comparison to a wild type strain. Very particular preference is given to strains in which at least one of these enzymes has been completely inactivated.

The cultivation of the cells during the L-cysteine production is carried out under aerobic growth conditions. The oxygen may be introduced into the culture in various ways, as for example by shaking the culture vessel by means of a shaking device. If the cultivation is carried out in a fermenter, either air or pure oxygen or a mixture of these gases can be blown into the culture. In order to ensure an adequate oxygen supply to the cells, the fermentation may also be carried out under pressure (e.g. at 0.5-1.2 bar excess pressure), whereby the solubility of oxygen in the medium is increased. In a stirred tank fermenter, the oxygen introduced is additionally dispersed by a stirrer in the medium, thereby increasing the availability of oxygen to the cells.

The oxygen dissolved in the medium is preferably measured continuously during the fermentation by means of a probe. This may be done, for example, with an optical sensor or a chemical sensor (Clark cell). The measured $O_2$ saturation of the medium is continuously adjusted to the predetermined nominal value.

If the actual value deviates from the nominal value, then either the gas supply or the stirring speed, or both, is adjusted by an automatic control circuit such that the $O_2$ saturation is again restored to the nominal value. In this manner, the oxygen content can be maintained in the culture throughout the whole fermentation period at a desired value.

The oxygen measuring probe is calibrated before the start of the fermentation to limiting values of 0% and 100% $O_2$ saturation in still non-inoculated medium. This is done expediently at the subsequent fermentation temperature.

Before the probe can be calibrated to 0% $O_2$ saturation, the entire oxygen still present must first be expelled from the medium. This is done automatically during the in situ sterilization of the fermentation medium in the fermenter or may be carried out by purging the medium with pure nitrogen at a stirring speed of 20% of the maximum possible stirring speed. The calibration of the probe to 100% $O_2$ saturation is generally carried out under the oxygen supply conditions existing at the start of the fermentation (initial conditions), i.e. at 40% of the maximum possible gas supply and at 20% of the maximum possible stirring speed. The calibration of the probe to 100% is carried out only when the oxygen content has reached a constant value under the chosen conditions.

The oxygen content during the production phase of the L-cystine fermentation must be maintained below 40±3% $O_2$ saturation, preferably below 30±3%, particularly preferably below 20±3%, especially preferably below 10±3%.

Preferred carbon sources are sugar, sugar alcohols, organic acids or sugar-containing plant hydrolyzates. Particularly preferred carbon sources used in the method according to the invention are glucose, fructose, lactose, glycerol or mixtures comprising two or more of these compounds.

The carbon source is preferably added to the culture such that the level of the carbon source in the fermenter during the cysteine production phase does not exceed 10 g/l. Preference is given to a maximum concentration of 2 g/l, particularly preferably 0.5 g/l, especially preferably 0.1 g/l.

The N sources used in the method according to the invention are preferably ammonia, ammonium salts or protein hydrolyzates. When using ammonia as correction means for pH stabilization, this N source is regularly replenished during the fermentation.

Salts of the elements phosphorus, chlorine, sodium, magnesium, nitrogen, potassium, calcium, iron and, in traces (i.e. in μM concentrations), salts of the elements molybdenum, boron, cobalt, manganese, zinc and nickel may be added as further media additions.

In addition, organic acids (e.g. acetate, citrate), amino acids (e.g. isoleucine) and vitamins (e.g. B1, B6) may be added to the medium.

The complex nutrient sources used may include e.g. yeast extract, corn steep liquor, soy flour or malt extract.

The incubation temperature for mesophilic microorganisms such as $E.\ coli$ or $P.\ ananatis$ is preferably 15-45° C., particularly preferably 30-37° C.

The pH of the fermentation medium during the fermentation is preferably in the pH range of 5.0 to 8.5 and particularly preferred is a pH of 7.0.

For producing L-cysteine and L-cysteine derivatives, a sulfur source must be fed in during the fermentation. In this case, preference is given to using sulfates or thiosulfates.

Microorganisms fermented according to the method described secrete L-cysteine and compounds derived therefrom into the fermentation medium with high efficiency, in a batch or fed batch process following a growth phase, over a period of eight to 150 hours.

After the fermentation, the L-cystine present as a precipitate may be separated from the remaining constituents of the culture broth by known methods, for example, using a decanter.

The following steps may be carried out for further purification of the crude product:
  dissolution of the crude product with a mineral acid
  clarification of the crude product solution by centrifugation or filtration
  discoloration of the solution
  precipitate crystallization The reduction of L-cystine to L-cysteine may be carried out, for example, by an electrochemical process as described in EP0235908.

The examples below further illustrate the invention.

EXAMPLE 1

Generation of Cysteine Production Strains

The wild type strains $E.\ coli$ W3110 (ATCC 27325) and $P.\ ananatis$ (ATCC 11530) were transformed in each case with the plasmid pACYC184/cysEX-GAPDH-ORF306 (disclosed in example 2 of U.S. Pat. No. 5,972,663A) by electroporation as described in U.S. Pat. No. 5,972,663A. The plasmid pACYC184/cysEX-GAPDH-ORF306 comprises, in addition to the replication origin and a tetracycline resistance gene, also the cysEX allele, which codes for a serine O-acetyltransferase having a reduced feedback inhibition by L-cysteine and also the efflux gene ydeD (ORF306), of which the expression is controlled by the constitutive GAPDH promoter.

The selection of plasmid-bearing cells was conducted on LB agar plates containing 15 mg/l tetracycline.

After a further plasmid isolation using the QIAprep Spin Plasmid Kit (Qiagen GmbH) and a restriction analysis, the desired transformants, i.e. cells, which have taken up the plasmid pACYC184/cysEX-GAPDH-ORF306, were isolated and were used in the fermentation, as is described in example 2.

EXAMPLE 2

Cultivation of Cysteine Production Strains at Different Oxygen Saturation

Preculture 1 (Shaking Flask):
20 ml of LB-medium containing 15 mg/l tetracycline were inoculated in an Erlenmeyer flask (100 ml) with the respective strain ($E.\ coli$ W3110 pACYC184/cysEX-GAPDH-ORF306 or $P.\ ananatis$ pACYC184/cysEX-GAPDH-ORF306) and were incubated for seven hours on a shaker (150 rpm, 30° C.)

Preculture 2 (Shaking Flask):
Subsequently, preculture 1 was completely transferred into 100 ml of SM1-medium (12 g/l $K_2HPO_4$, 3 g/l $KH_2PO_4$, 5 g/l $(NH_4)_2SO_4$, 0.3 g/l $MgSO_4 \times 7\ H_2O$, 0.015 g/l $CaCl_2 \times 2\ H_2O$, 0.002 g/l $FeSO_4 \times 7\ H_2O$, 1 g/l $Na_3$ citrate$\times 2\ H_2O$, 0.1 g/l NaCl, 1 ml/l trace element solution consisting of 0.15 g/l $Na_2MoO_4 \times 2H_2O$, 2.5 g/l $H_3BO_3$, 0.7 g/l $CoCl_2 \times 6\ H_2O$, 0.25 g/l $CuSO_4 \times 5\ H_2O$, 1.6 g/l $MnCl_2 \times 4\ H_2O$, 0.3 g/l $ZnSO_4 \times 7\ H_2O$), which had been supplemented with 5 g/l glucose, 5 mg/l vitamin B1 and 15 mg/l tetracycline. The cultures were shaken in Erlenmeyer flasks (1 l) at 30° C. for 17 h at 150 rpm. Following this incubation, the optical density at 600 nm ($OD_{600}$) was between 3 and 5.

Main Culture (Fermenter):

The fermentation was carried out in fermenters of type BIOSTAT B from Sartorius Stedim. A culture vessel with a 2 l total volume was used. The fermentation medium (900 ml) comprises 15 g/l glucose, 10 g/l tryptone (Difco), 5 g/l yeast extract (Difco), 5 g/l $(NH_4)_2SO_4$, 1.5 g/l $KH_2PO_4$, 0.5 g/l NaCl, 0.3 g/l $MgSO_4 \times 7\,H_2O$, 0.015 g/l $CaCl_2 \times 2\,H_2O$, 0.075 g/l $FeSO_4 \times 7\,H_2O$, 1 g/l $Na_3$ citrate$\times 2\,H_2O$ and 1 ml of a trace element solution (see above), 0.005 g/l vitamin B1 and 15 mg/l tetracycline. The pH in the fermenter was adjusted at the start to 7.0 by pumping in a 25% $NH_4OH$ solution. During the fermentation, the pH was maintained at 7.0 by automatic correction using 25% $NH_4OH$. For the inoculation, 100 ml of preculture 2 was pumped into the fermentation vessel. The starting volume was therefore about 1 l. The cultures were stirred at the start at 400 rpm and were gassed at 2 vvm with compressed air sterilized via a sterile filter. The oxygen probe had been calibrated to 100% saturation under these starting conditions before the inoculation. The nominal value for the $O_2$ saturation during the fermentation was adjusted—depending on the experimental batch—to 50±5%, 40±5%, 30±5%, 20±5% or 10±5%. On falling of the $O_2$ saturation below the respective nominal value, a regulation cascade was initiated to restore the $O_2$ saturation again to the nominal value. Initially the gas supply was continuously increased (to max. 5 vvm) and then the stirring speed was continuously increased (to max. 1500 rpm).

The fermentation was carried out at a temperature of 30° C. After a fermentation time of 2 h, the feeding in of a sulfur source was carried out in the form of a sterile 60% sodium thiosulfate$\times 5\,H_2O$ stock solution at a rate of 1.5 ml per hour. Once the glucose content in the fermenter had fallen from an initial 15 g/l to ca. 2 g/l, a 56% glucose solution was continuously added. The feeding rate was adjusted so that the glucose concentration in the fermenter from that point did not exceed 2 g/l. The glucose determination was carried out using a glucose analyzer from YSI (Yellow Springs, Ohio, USA). The fermentation time was 48 hours. Thereafter, samples were taken and the L-cysteine content, and the content of the derivatives derived therefrom, in the culture supernatant (especially L-cysteine and thiazolidine), and in the precipitate (L-cystine), were each determined independently (see Table 1). For this purpose, the colorimetric test of Gaitonde was used in each case (Gaitonde, M. K. (1967), Biochem. J. 104, 627-633). It should be noted here that, under the strongly acidic reaction conditions of the test, not only free L-cysteine, but also the L-cysteine bound in the thiazolidine are together recorded and quantified. L-cystine dissolved in the culture supernatant is detected in the Gaitonde test also as L-cysteine following reduction with dithiothreitol (DTT) in dilute solution at pH 8.0. The L-cystine located in the precipitate had to be first dissolved in 8% hydrochloric acid before it could be quantified in the same manner.

TABLE 1

Content of L-cysteine and L-cysteine derivatives in the culture broth after 48 h

| Nominal $O_2$ saturation [%] | E. coli Cysteine content [g/l] after 48 h Supernatant[1] | E. coli Cysteine content [g/l] after 48 h Precipitate[2] | Proportion of cystine [%][3] | P. ananatis Cysteine content [g/l] after 48 h Supernatant[1] | P. ananatis Cysteine content [g/l] after 48 h Precipitate[2] | Proportion of cystine [%][3] |
|---|---|---|---|---|---|---|
| 50 ± 3 (comparative ex.) | 6.3 | 11.0 | 63.6 | 3.8 | 8.2 | 68.3 |
| 40 ± 3 | 5.1 | 12.3 | 70.7 | 3.7 | 9.1 | 71.1 |
| 30 ± 3 | 4.1 | 14.7 | 78.2 | 3.3 | 10.5 | 76.1 |
| 20 ± 3 | 2.7 | 16.4 | 85.9 | 2.6 | 12.8 | 83.1 |
| 10 ± 3 | 1.9 | 17.9 | 90.4 | 1.3 | 14.1 | 91.6 |

[1]Sum of the L-cysteine, L-cystine and thiazolidine dissolved in the supernatant
[2]L-cystine in the precipitate
[3]L-cystine in the precipitate as a proportion of total cysteine

The invention claimed is:

1. A method for producing L-cystine comprising fermenting a microorganism strain which produces L-cysteine in a fermentation medium, wherein the L-cystine precipitates in an amount of at least 70% (g/L) relative to the amount of total cysteine, and an $O_2$ saturation of the fermentation medium during L-cystine production is maintained at least at 1% and at most at 40±3%.

2. The method as claimed in claim 1, wherein the $O_2$ saturation during the formation of L-cystine is maintained below 30±3%.

3. The method as claimed in claim 1, wherein the microorganism strain used is a representative from the Enterobacteriaceae family.

4. The method as claimed in claim 3, wherein: (a) the microorganism strain either has a serine O-acetyltransferase, which has a feedback inhibition by L-cysteine reduced by at least a factor of 2 in comparison to a corresponding wild type enzyme, or (b) the microorganism strain has a cysteine export increased by at least a factor of 2 by overexpression of an efflux gene in comparison to a wild type strain.

5. The method as claimed in claim 4, wherein the microorganism strain additionally has a 3-phosphoglycerate dehydrogenase having a feedback inhibition by L-serine reduced by at least a factor of 2 in comparison to the corresponding wild type enzyme.

6. The method as claimed in claim 1, wherein oxygen is introduced into the fermentation medium by shaking the culture vessel by use of a shaking device or by blowing in air or pure oxygen or a mixture of these gases.

7. The method as claimed in claim 1, wherein a carbon source is added to the fermentation medium such that a level of the carbon source in a fermenter during cysteine production does not exceed 10 g/l.

8. The method as claimed in claim 1, wherein an incubation temperature is 15-45° C., and a pH of the fermentation medium during fermentation is at a pH in a range of 5.0 to 8.5.

9. The method as claimed in claim 1, wherein a sulfur source is fed in during fermentation.

10. The method as claimed in claim 2, wherein the $O_2$ saturation during the formation of L-cystine is maintained below 10±3%.

11. The method as claimed in claim 10, wherein the microorganism strain used is a representative from the genera *Escherichia* or *Pantoea*.

12. The method as claimed in claim 11, wherein: (a) the microorganism strain either has a serine O-acetyltransferase, which has a feedback inhibition by L-cysteine reduced by at least a factor of 2 in comparison to a corresponding wild type enzyme, or (b) the microorganism strain has a cysteine export increased by at least a factor of 2 by overexpression of an efflux gene in comparison to a wild type strain.

13. The method as claimed in claim 12, wherein the microorganism strain additionally has a 3-phosphoglycerate dehydrogenase having a feedback inhibition by L-serine reduced by at least a factor of 2 in comparison to the corresponding wild type enzyme.

14. The method as claimed in claim 13, wherein oxygen is introduced into the fermentation medium by shaking the culture vessel by use of a shaking device or by blowing in air or pure oxygen or a mixture of these gases.

15. The method as claimed in claim 14, wherein a carbon source is added to the fermentation medium such that a level of the carbon source in a fermenter during cysteine production does not exceed 10 g/l.

16. The method as claimed in claim 15, wherein an incubation temperature is 30-37° C., and a pH of the fermentation medium during fermentation is 7.0.

17. The method as claimed in claim 16, wherein a sulfate or a thiosulfate is fed in during fermentation.

\* \* \* \* \*